United States Patent [19]

Yamada et al.

[11] 4,353,984

[45] Oct. 12, 1982

[54] COMPOSITION AND TEST PIECE FOR MEASURING GLUCOSE CONCENTRATION IN BODY FLUIDS

[75] Inventors: Shigeki Yamada, Jyoyo; Takao Yamamoto, Kyoto, both of Japan

[73] Assignee: Kabushiki Kaisha Kyoto Daiichi Kagaku, Kyoto, Japan

[21] Appl. No.: 205,367

[22] PCT Filed: Jan. 4, 1980

[86] PCT No.: PCT/JP80/00004

§ 371 Date: Sep. 2, 1980

§ 102(e) Date: Aug. 28, 1980

[87] PCT Pub. No.: WO80/01389

PCT Pub. Date: Jul. 10, 1980

[30] Foreign Application Priority Data

Dec. 31, 1978 [JP] Japan .................................. 53-164968

[51] Int. Cl.³ ..................... G01N 33/66; G01N 33/52

[52] U.S. Cl. ..................................... 435/14; 23/230 B; 23/901; 252/408; 422/56; 435/28; 435/805

[58] Field of Search ................ 435/14, 805; 252/408; 422/56; 23/901

[56] References Cited

U.S. PATENT DOCUMENTS

| | | | |
|---|---|---|---|
| 3,092,465 | 6/1963 | Adams | 435/14 |
| 3,598,704 | 8/1971 | Dahlqvist | 435/14 |
| 3,971,702 | 7/1976 | Maekawa | 435/14 |
| 4,066,408 | 1/1978 | Jonsson | 435/14 X |
| 4,318,985 | 3/1982 | Bauer | 23/901 X |

Primary Examiner—Sidney Marantz
Attorney, Agent, or Firm—Darby & Darby

[57] ABSTRACT

A composition and test piece or dipstick for measuring the glucose concentration in body fluids such as urine, spinal fluid and blood. The composition includes a glucose oxidase, a peroxidase a N,N'-tetramethyldiaminophenylmethane and guaiac.

11 Claims, 3 Drawing Figures

COMPOSITION AND TEST PIECE FOR MEASURING GLUCOSE CONCENTRATION IN BODY FLUIDS

DESCRIPTION

1. Field of the Invention

This invention relates to an improvement of the test piece for measuring the concentration of glucose being contained in the body fluid such as urine, spinal fluid, blood, and the like.

2. Description of the Prior Art

The measurement of the concentration of glucose in the body fluid is of importance in the clinical examination, and it is particularly necessary to detect the glucose in urine, and measure its concentration, for the early detection, diagnosis, and control of diabetes and other diseases coexistent therewith.

As a test method to attain such objects, it is preferable to measure rapidly and easily without using any instrument, and furthermore it must have the sufficient exactitude helpful to the diagnosis.

A test piece for glucose has been used heretofore for these purposes. This test piece is made by dipping an absorptive material into a solution containing glucose oxidase, peroxidase, oxidizable chromogen and a buffer agent, and then by drying it. If the thus produced test piece is dipped into the urine, it will be colored corresponding to the concentration of glucose in the urine, upon the principle which is expressed schematically below. The detection and measurement of glucose become practicable through the judgement of this chroma.

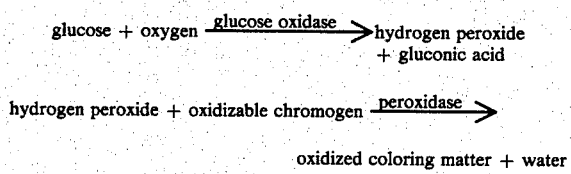

As an oxidizable chromogen, there has been used heretofore a chromogen indicator such as orthotolidine, benzidine, orthodianisidine and the like. However, in the case of detecting or measuring glucose in the urine through the application of a test piece made with the use of these indicators, the color reaction will be affected by the specific gravity (the degree of concentration or dilution) of the urine, otherwise by reducing medical substance such as vitamin C (ascorbic acid) coexisting together with the urine, which entail a serious defect incurring big errors in the measurement. Not only that, these kinds of chromogen indicators have carcinogenicity, and therefore encounter a problem for reasons of safety and the sanitation of persons engaged in their production and furthermore their users.

In order to eliminate these defects, there is disclosed in the Japanese Patent Publication No. 39558 of 1975 a test piece for semi-determining the glucose which is coated on its surface with a hydrophobic film-forming polymer such as cellulose ether and ester while applying a water soluble iodine salt as a chromogen. As being understood from the above, this invention uses a water soluble iodine salt as a chromogen. In order to make this chromogen function effectively as an indicator material, the test piece according to this patent is coated with a hydrophobic film-forming polymer, whereby it claims to be able to prevent the harmful influence from vitamin C (ascorbic acid).

It was proved, however, in the light of the thorough investigation conducted by the author of our invention from an independent standpoint that, as compared with the case where usual chromogen indicators are used, the test piece disclosed in the above-mentioned patent has several defects such that it is 2-3 times longer in the reaction time, that its detection sensitivity is poor to the existence of glucose in the urine (more than 100 mg/dl), and that it is wanting in the stability of long-term conservation due to the lack of stability of water soluble iodine salt impregnated in that test piece.

Through the elimination of the above-mentioned defects, our present invention has for its object the provision of such a kind of test piece for measuring the glucose in the urine quickly and easily, where its measured result is not affected by the composition of the examined body fluid, its detection sensitivity is sufficient for clinical examination, is excellent in the stability of conservation, and can avoid the use of any carcinogenic chromogen.

SUMMARY OF THE INVENTION

Our invention is one where the test piece for measuring the glucose in the body fluid has its substrate impregnated or painted with an enzymatic species displaying glucose oxidase activity, a substance having peroxidase-like activity, oxidable chromogen, and is buffer agent, wherein guaiac fat and tetrabase or the mixture of their derivatives used as an oxidizable chromogen, whereby the aforementioned object of the invention can be attained satisfactorily.

Furthermore, by making the test piece contain polyvinylbutyral, our present invention is able to hold down the undesired influence of abnormally large levels of vitamin C (ascorbic acid) in, the body fluid; therefore the use of the aforesaid substance (polyvinylbutyral) enables the object of this invention to be achieved more perfectly.

BEST MODE FOR CARRYING OUT THE INVENTION

Figure 1:
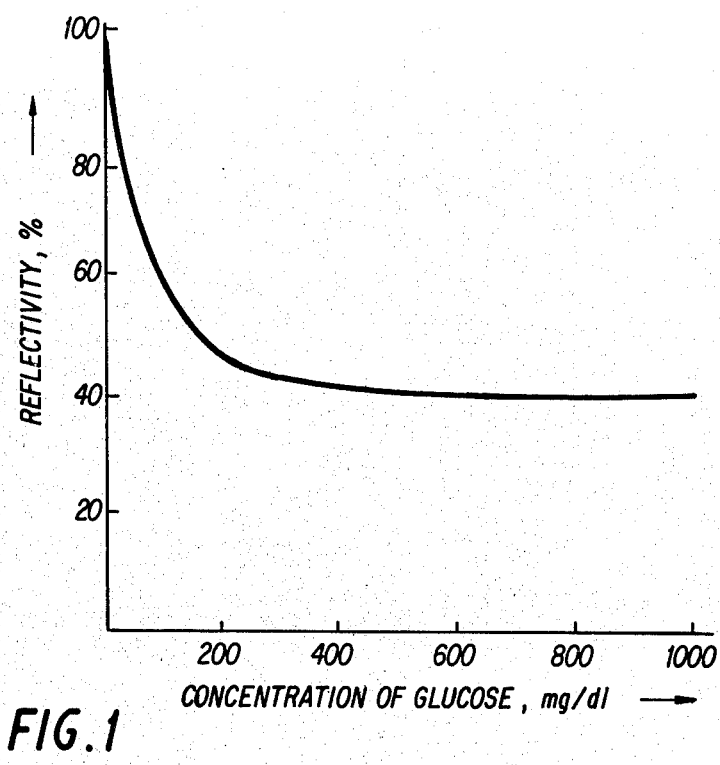
FIG. 1 is a graph of standard curve showing the correlation between the reflectivity and the concentration of glucose in the urine taken from the test piece for measuring the glucose which is made by the use of the guaiac fat as an oxidizable chromogen.

In order to explain our invention in further details, description will now be made with reference to the examples and to the accompanying drawings.

The test piece of our invention is made by making its substrate be impregnated or painted with enzymatic species displaying glucose oxidase activity, substances having peroxidase-like activity, a buffer agent, and guaiac fat and tetrabase as a chromogen, and further, as occasion demands, with polyvinylbutyral. When thus produced and the test piece is dipped into the body fluid which is to be examined, or else the latter is painted on the former, it presents a chroma correspondingly to the concentration of glucose. The test piece of our invention, as such, is not subject to the influence of the composition of the examined body fluid, does not contain any carcinogenic substance, has excellent detection sensitivity and stability of conservation, and thereby can eliminate various defects of conventional techniques.

The principle of coloration of the test piece of our invention will be expressed schematically below. Glucose oxidase oxidizes specifically glucose to produce hydrogen peroxide and gluconic acid of a quantity correspondent to the concentration of glucose. Then this hydrogen peroxide oxidizes guaiac fat and tetrabase by the action of peroxidase to form an oxidizing coloring matter, as a result presenting the concentration of glucose. By observing the chroma with the naked eye or by means of a light reflectometer, it becomes possible to detect and measure the glucose in the examined body fluid.

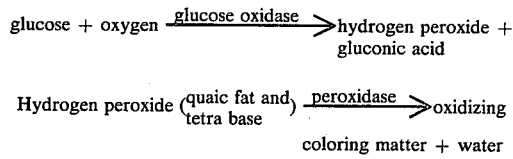

In conventional arts, there have been used chromogen indicators such as orthotolidine, benzidine, orthodianisidine and the like. These kinds of indicators have high color sensitivity, so that they are capable of detecting the existence of a required glucose to the full in the presence of a small quantity of hydrogen peroxide generated by the action of glucose oxidase and also in the presence of a small quantity of peroxidase, and besides they can present the chroma correspondent to the concentration of glucose. However, if some reducing medicinal substances such as vitamin C and the like should be present in the body fluids, for example, urine which is to be examined, they will come to consume hydrogen peroxide of a small quantity produced by the action of glucose oxidase, so that there may occur no coloration or, if any, a chroma lower than normal, which will lead to serious errors in measurements. What is more, in the urine is contained uric acid resulting from the metabolism. Since this uric acid is also a reducing substance, it presents a chroma lower than normal in the case of the concentrated urine in which the specific gravity of examined urine is larger than usual, while on the other hand it presents a higher chroma in the case of the dilute urine. This leads likewise to serious errors in measurements.

The authors of our invention found that in the case of glucose oxidase of a quantity necessary to the color reaction on the test piece for glucose made by conventional techniques, the oxidative activity of glucose oxidase is affected by the concentration of sodium chloride contained in the urine, that in the concentration range of sodium chloride contained in the regular urine, the concentration of sodium chloride is inversely proportional to the activity of glucose oxidase, and that if glucose oxidase is used in a large quantity, the influence of the concentration of sodium chloride can be held down.

The authors of this invention also found that the hydrogen peroxide produced by the action of glucose oxidase is consumed by reducing substances, in consequence of which the measurement errors take place, that in order to prevent such kind of inconvenience, it is necessary to make hydrogen peroxide be produced in a greater quantity, whereby the consumption rate of it comes to be held down, and that paying attention to the before-mentioned correlation between the concentration of sodium chloride and the activity of glucose oxidase, it is proper that glucose oxidase should be applied in a large quantity to the test piece.

However, as previously stated, chromogen indicators such as orthotolidine, benzidine or orthodianisidine have a good coloration sensitivity and accordingly, if glucose oxidase is used in a large quantity, they present the sensitivity of detection to glucose more than required, so that the range of measurements becomes narrow. It follows from this that the test piece produced here is unsuitable for clinical examination. Thereupon, the authors took notice of the necessity of using another chromogen having the lower coloration sensitivity.

Figure 2:
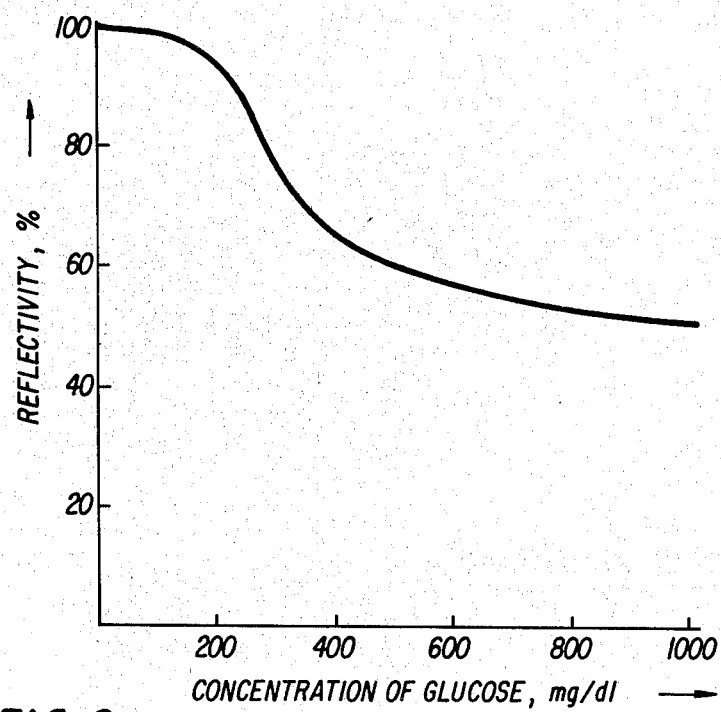
FIG. 2 is a graph of another standard curve of the same sort taken from the test piece for measuring the glucose which is made by the use of only tetrabase as an oxidizable chromogen.

Then the authors, who had been seeking for an oxidable chromogen having a coloration sensitivity low to the moderate degree and, if possible, being non-carcinogenic, finally thought of guaic fat well-known in this field. When they applied this fat, in accordance with the aforesaid purpose, to the test piece and tested thus produced test piece by using a urine sample which contained glucose of a known concentration, then it presented a practically same color independently from the concentration of glucose at more than about 200 mg/dl of the latter. When the standard curve graphing the correlation between the reflectivity and the concentration of glucose in the urine was constructed through the use of a light reflectometer having a measuring wavelength of 620 nm correspondent to the hue generated from the oxidized guaiac fat, it was as shown in FIG. 1. Then the authors thought that it should do better if some oxidable chromogen having the coloration sensitivity a little lower than guaiac fat and also having an oxidation-caused hue of the same degree as the hue of guaiac fact would be used in combination with guaiac fat. They eagerly searched for such kind of oxidable chromogen, until they recognized that it is tetrabase that is the one and only optimum substance. Just for information, there is graphed in FIG. 2 the standard curve showing the correlation between the reflectivity and the concentration of glucose in the urine on the test piece made by using only tetrabase as an oxidizable chromogen. In the case of the test piece made by using the tetrabase, the coloration starts from the concentration of glucose of about 200 mg/dl, in the course of which the respective chromas correspondent to each of the concentration of glucose are obtainable in the ranges of 200 to 1000 mg/dl.

Figure 3:
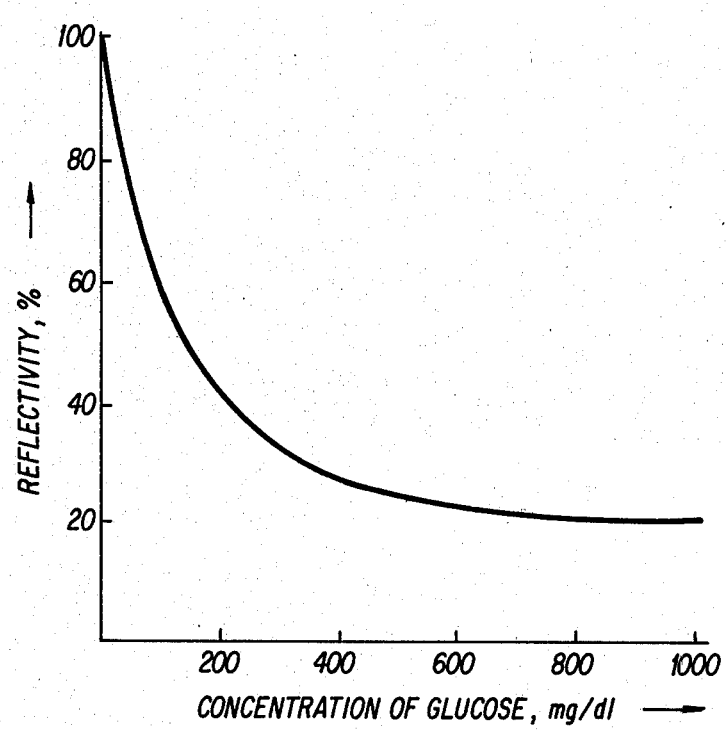
FIG. 3 is a graph of a standard curve of the same sort taken from the test piece used in Example 1 of this invention.

From the above-mentioned, the authors guessed that the object of this invention would be achieved by using the mixture of guaiac fat and tetrabase as oxidizable chromogen. The results of the experiments of various sorts and kinds turned out even as they guessed: It was proved that the mixing ratio of both is practicable at 1:1 to 1:10, but the optimum ratio is between 1:2 to 1:4. For example, there is shown in FIG. 3 the standard curve graphing the correlation between the reflectivity and the concentration of glucose in the urine on the test piece of which the mixing ratio is at 1:3. In the case of this test piece, the measurement can be made in the ranges of 0 to 1000 mg/dl of the concentration of glucose in the urine, which enables the glucose to be detected at the sensitivity necessary for clinical examination.

In this way, if guaiac fat and tetrabase are used jointly as an oxidizable chromogen, and glucose oxidase is made to be contained in the test piece in a large quantity, they are scarcely subject to any influence even in the range of the fluctuation of specific gravity of the examined urine taken from the patient under normal conditions, and also in the range of the content of the reducing substances such as vitamin C or glutathione coexisting with the urine as medicinal matters, thereby making possible the accurate measurement of glucose. For all that, there is a very rarely special case that no less than 50 to 100 mg/dl of vitamin C coexists with the urine in the examined urine of the patient directly after the inoculation of a large quantity of vitamin C.

The authors made a further study with the purpose of coping with the coexistence of an large quantity of vitamin C in such a very rarely special case, as a result of which they found that it was possible to completely eliminate the influence of vitamin C by making the test piece according to the invention contain polyvinylbutyral. But, on the other hand, the application of organic synthetic polymers such as polyvinylpyrrolidone, polyvinyl alcohol, ethyl cellulose, and the like, all having the same character as the above polyvinylbutyral likewise to the test piece of our invention exhibited any effectiveness. It was only polyvinylbutyral that displayed a remarkable effect. Though it is unclear why it is so, it is thinkable probably because the reductive substances such as vitamin C and the like would be sustained on the surface of the test piece, so that their participation in the color reaction might be held down in this case.

As mentioned above, the object of our invention can be achieved not only by using the mixture of guaiac fat and tetrabase as an oxidable chromogen, but also further completely by additional applying polyvinylbutyral.

The test piece of our invention for use in the measurement of glucose contains enzymatic species displaying the glucose oxidase activity, substances having the peroxidase-like activity, guaiac fat, tetrabase, buffering agent and polyvinylbutyral. As the enzimatic species displaying the glucose oxidase can be used any substance irrespective of its kind so long as it has the enzimatic action capable of generating the hydrogen peroxide by specifically oxidizing the glucose. As the substances having the peroxidase-like activity, it is possible to use any kind of substance if only it has the enzimatic activity able to oxidize both guaiac fat and tetrabase with the help of hydrogen peroxide. As a buffering agent, any substance will do so long as it has the effect of maintaining a suitable pH somewhere in the range of pH 3.0 to 7.5. Any polyvinylbutyral is available if only it is in the range of 200 to 1500 degrees of polymerization. Butyral resins as an industrial product are copolymers of vinylbutyral, vinyl acetate, and vinyl alcohol—such kinds of polyvinylbutyral derivatives are fit for use. For guaiac fat, usable are guaiac resin as the natural resin, or guaiaconic acid, guaiarethene acid, and guaiac acid as the main ingredients of the guaiac resin. Tetrabase is a popular name of N,N'-tetramethyl-4,4'-diaminodiphenylmethane. Its derivative, N,N'-tetramethyl-3,3'-diaminodiphenylmethane, is also available. Furthermore, various sorts of additives such as, for example, a protective agent, a concentrating agent, a wetting agent, surface active agent and others, and also an inert dyestuff for giving some ground color—any of these may be compounded to form the test piece according to the invention.

In order to produce the test piece of our invention, as a start a solution is made, which contains glucose oxidase, peroxidase, and the buffering agent out of the before-mentioned composition. Into this solution is dipped an absorptive material made of a filter paper and the like. After that, it is taken out therefrom and is left to get dry. And this is dipped again into the solution which contains guaiac fat, tetrabase and polyvinylbutyral, and left to get dry. Or again it is possible to use except the above-mentioned absorptive substrate some film such as made of polyvinyl chloride as it is in the capacity of a substrate. In this case, the solution containing the aforesaid components is prepared by compounding thereto further adhesives which aids the adhesion of the above compositions to the film, silica gel which promotes the permeation of the examined body fluid thereinto, and porous particles such as titanium oxide granules. After this solution has been painted on the film, it is left to dry, when the test piece is obtainable.

When thus produced test piece for the measurement of glucose is dipped into the body fluid which is to be examined, otherwise the latter is painted on the former, then there is exhibits the chroma correspondent to the concentration of glucose. If a standard simple colorimetric table of a certain form compiled beforehand correspondingly to the actual variations of the concentration of glucose is prepared near at hand, it is possible to semi-measure easily the glucose by comparing the colored chroma observed with the naked eye with the above standard colorimetric table. And further, if there have been prepared different kinds of standard curves showing the correlations between the reflectivities and the concentrations of glucose being based on the results of the measurements of the reflectivities of the test pieces by means of a reflectometer having the measuring light wavelengthes corresponding to the colored hues, while using the standard solutions having the varying concentrations of glucose, it is also possible to estimate the glucose.

Now, a few preferred examples are given below, but the scope of the invention is not to be construed to be restricted only to them.

EXAMPLE 1

800 mg of sodium alginate (1000 cps), 3.3 g of citric acid.H$_2$O, and 8.7 g of citric acid-3-sodium.2-H$_2$O are added to 100 ml of prepurified water to be dissolved by stirring, whereto is further added 600 mg of glucose oxidase (100 U/mg), and 100 mg of peroxidase (100 U/mg), which is likewise dissolved by slowly stirring. In such a manner is made the solution for the first stage treatment. After a filter paper for chromatographing is dipped satisfyingly in this solution, it is pulled out therefrom to be left to dry at 50° C. for 1.5 hours.

Then, 0.5 g of guaiac fat and 1.5 g of tetrabase are added to 100 ml of acetone and are dissolved to obtain the solution for the second stage treatment. Into this solution is dipped again the test piece which have finished the first stage treatment and is left to dry up at 45° C. for 30 minutes. With this is completed the final finishing of the test piece.

The test piece prepared in this way is cut in bits. Each separated bit is stuck on one end of a rectangular strip-shaped plastic film by the use of a double-faced adhesive tape. These bits are kept in a hermetically sealed receptacle containing silica gel as a desiccant, thereby being able to be conserved in stable form for more than a year. By doing so, they can be conveniently used taking out therefrom whenever being needed.

When this piece is pulled up directly it has been dipped into the examined urine, it colors blue. The chroma in this case is corresponding to the then concentration of glucose, so that the semi-measurement of glucose is feasible through its color comparison by the naked eye in reference to the standard colorimetric table made out beforehand.

Aside from this, it is possible to measure the glucose in light of the standard curve (FIG. 3) showing the correlation between both the reflectivity measured at the time of the coloration of the test piece through the use of a reflectometer which irradiates the surface of the test piece with the monochromatic light of 620 nm to measure its reflected rays, and the concentration of glucose, which standard curve has been worked out in advance by the use of the various sorts of standard solution of glucose whose varying concentration degree are known.

EXAMPLE 2

To the buffering solution which has been made in advance by adding 4.7 g of potassium phosphate ($K_2HPO_4$) and 3.8 g of sodium phosphate (Na $H_2PO_4H_2O$) to 100 ml of prepurified water and by stirring them all, 1.0 g of gelatine is added, stirred thoroughly, and dissolved, whereto 800 mg of glucose oxidase (110 U/mg) and 105 mg of peperoxidase (130 U/mg) are added, stirred slowly, and dissolved. In this manner is preparable the solution for the first stage treatment. Into this solution is dipped the qualitative filter paper, which is then pulled out and left to dry at 45° C. for two hours.

The solution for the second stage treatment is made by adding 1.0 g of guaiac fat, 1.5 g of tetrabase, 0.5 g of TWEEN 20 (trade name of an interfacial activator), and 2.5 g of polyvinylbutyral (700 degrees of polymerization) all to the mixed solvent of acetone-toluene ethyl alcohol in the ratio of 1:1:2, and by being made to be dissolved. Into this solution is dipped the test piece having finished the first stage treatment for the second time. With the drying at 45° C. for 60 minutes is completed finally the fabrication of the test piece of our invention.

The conservation and way of use is also in this test piece the same as in Example 1.

In the above, reference has been made to some preferable examples for working of the present invention. However, modification and variation is possible in the substances constituting the test piece: For example, any enzyme can be applied regardless of its origin if it displays the glucose oxidase activity. In the same way, as substances having the peroxidase-like activity, hemoglobin, urohemin, and the like can be substituted for peroxidase having been given in the examples. As a buffering agent can be used, along with the ones such as originating from citric acid or phosphoric acid, a mixture of citrate and phosphate, tartrate, amino acid salt, and the like, as long as they are substances having an effect of maintaining the pH value in the range of pH 3.0 to 7.5. In the place of guaiac fat which comes to hand in the form of a natural resin under normal conditions, it is possible to use guaiaconic acid, guaiarethene acid, or guaiac acid, which each form the principal constituents of guaiac fat. Referring to tetrabase and polyvinylbutyral, any derivative of them can be used as substitute for the ones shown in the example so long as it is changeless in the fundamental properties. It is further admissible to employ carboxymethylcellulose, soluble starch, cow-serum albumin and the like as protective agent or concentrating agent in place of gelatine and sodium alginate; polyethylene glycol and polyvinylpyrrolidone as wetting agent; and cationic or anionic surface active agent and the like in the capacity of a surface active agent beside the non-ionized one such as "TWEEN 20" mentioned above. For the inert dyestaff giving a ground color, the food coloring matter: yellow 4, for example, can be compounded if desired. With regard to the material of the test piece, the working of the invention can be conducted, separately from the previously-mentioned absorptive material, such as made of filter paper, cloth, or wood piece, by additionally painting some suitable adhesive or porous particles as constituent substance of the test piece directly on the material such as a film, for example, made of polyvinyl chloride or polyester.

To examine the effect of this invention, we made an investigation by comparison on the test piece of glucose made by conventional technique in which orthotolidine is adopted as chromogen, on one hand and on the test piece shown in Examples 1 and 2 of our invention, on the other, in relation to the specific gravity of the urine, and to the influence of vitamin C coexistent with glucose in the urine. The results were as follows:

As a start, four kinds of urine (A, B, C, and D) having different specific gravities were collected, which were all tested with the use of two sorts of urine samples made by adding glucose in such a method that their glucose contents might become 100 mg/dl and 400 mg/dl, respectively. In this way, their respective reflectivities were measured by using the reflectometer whose measuring wavelength was correspondent to the monochromatic light of 620 nm degrees of coloration of the test piece. In this test, the reaction time was set to be 40 seconds. As positively proved from the results entered in Table 1, the test piece made by conventional techniques was seriously affected by the specific gravity of the urine, while on the contrary, the test piece according to Example 1 and 2 of the invention has been scarcely subject to the influence similar to the above.

TABLE 1

| Concentration of glucose of sample | Test object | A | B | C | D |
|---|---|---|---|---|---|
| | Specific gravity | 1.007 | 1.019 | 1.025 | 1.043 |
| 100mg/dl | Conventional manufacture | 21.3 | 55.5 | 66.4 | 87.2 |
| | Example 1 | 55.2 | 55.7 | 57/1 | 58.6 |
| | Example 2 | 56.6 | 59.8 | 58.0 | 57.3 |
| 400mg/dl | Conventional manufacture | 16.9 | 22.4 | 53.8 | 75.2 |
| | Example 1 | 24.3 | 26.9 | 27.1 | 29.2 |
| | Example 2 | 31.5 | 31.3 | 33.3 | 34.7 |

Note:
Numerical values in the table show the reflectivities.

The next test was conducted in like method with the use of the two sorts of urine samples which were prepared by adding glucose to the urines of an average specific gravity in such a method that their glucose contents might become 100 mg/dl and 400 mg/dl, and furthermore by adding vitamin C to the respective urine samples so that their coexistent amounts each should be 10, 30, 50, and 100 mg/dl. The results of measuring their reflectivities will be given in Table 2 in the same way as in the former test. From this, it was confirmed that the test piece made by conventional techniques was seriously affected by vitamin C, while the test piece of Example 1 of this invention was scarecely influenced of vitamin C of up to 50 mg/dl, and the test piece of Example 2 was hardly influenced by vitamin C of up to 100 mg/dl.

TABLE 2

| Concentration of glucose of sample | Concentration of vitamin C of sample | 0 | 10mg/dl | 30mg/dl | 50mg/dl | 100mg/dl |
|---|---|---|---|---|---|---|
| 100mg/dl | Conventional manufacture | 55.5 | 62.6 | 76.5 | 89.6 | 93.1 |
| | Example 1 | 55.7 | 56.0 | 76.5 | 89.6 | 76.1 |
| | Example 2 | 59.8 | 58.6 | 59.1 | 61.2 | 62.3 |
| 400mg/dl | Conventional manufacture | 22.4 | 34,41 | 39.1 | 59.6 | 89.3 |
| | Example 1 | 26.9 | 26.5 | 29.1 | 28.5 | 49.6 |
| | Example 2 | 31.3 | 30.0 | 32.4 | 32.9 | 36.8 |

Note:
Numerical values in the table show the reflectivities.

We claim:

1. A diagnostic composition which comprises a glucose oxidase, a peroxidase, a N,N'-tetramethyldiaminophenylmethane and guaiac.

2. A composition as claimed in claim 1 wherein said N,N'-tetramethyldiaminophenylmethane comprises N,N'-tetramethyl 3,3'-diaminophenylmethane.

3. A composition as claimed in claim 1 wherein said N,N'-tetramethyldiaminophenylmethane comprises N,N'-tetramethyl-4,4'-diaminophenylmethane.

4. A composition as claimed in claim 3 wherein said guaiac and said N,N'-tetramethyl 4,4'-diaminophenylmethane are present in said composition in a weight ratio of from about 1:1 to about 1:10.

5. A composition as claimed in claim 4, wherein said guaiac and said N,N'-tetramethyl 4,4'-diaminophenylmethane are present in a weight ratio of from about 1:2 to about 1:4.

6. A composition as claimed in claim 5 further comprising a buffering agent.

7. A composition as claimed in claim 4 or 5 wherein said guaiac is selected from the group consisting of guaiac resin, guaiaconic acid, guaiarethene acid and guaiac acid.

8. A composition as claimed in any of claims 3-5 further comprising polyvinylbutyral.

9. A test piece comprising a substrate supporting a diagnostic composition which comprises a glucose oxidase, a peroxidase, guaiac and a N,N'-tetramethyldiaminophenylmethane.

10. A test piece as claimed in claim 9 wherein said N,N'-tetramethyldiaminophenylmethane comprises N,N'-tetramethyl-4,4'-diaminophenylmethane.

11. A test piece as claimed in claim 10 further comprising polyvinylbutyral.

* * * * *